United States Patent [19]

Duplan et al.

[11] Patent Number: 5,304,150

[45] Date of Patent: Apr. 19, 1994

[54] RETRACTABLE NEEDLE FOR USE WITH SYRINGE

[75] Inventors: Nancy Duplan; Carlton E. Duplan, both of San Marcos, Calif.

[73] Assignee: Duplan Industries, San Marcos, Calif.

[21] Appl. No.: 903,617

[22] Filed: Jun. 24, 1992

[51] Int. Cl.⁵ ............................... A61M 5/00
[52] U.S. Cl. ......................... 604/195; 604/110
[58] Field of Search ............ 604/110, 195–198, 604/218, 239, 240, 243, 194

[56] References Cited

U.S. PATENT DOCUMENTS

| | | | |
|---|---|---|---|
| 4,650,468 | 3/1987 | Jennings, Jr. | 604/110 |
| 4,897,083 | 1/1990 | Martell | 604/192 |
| 4,900,307 | 2/1990 | Kulli | 604/110 |
| 4,955,869 | 9/1990 | Bin | 604/195 |
| 4,966,592 | 10/1990 | Burns et al. | 604/198 |
| 4,969,877 | 11/1990 | Kornberg | 604/195 |
| 4,978,340 | 12/1990 | Terrill et al. | 604/195 |
| 4,985,021 | 1/1991 | Straw et al. | 604/198 |
| 5,047,016 | 9/1991 | Dolgin et al. | 604/110 |
| 5,053,018 | 10/1991 | Talonn et al. | 604/198 |
| 5,057,087 | 10/1991 | Harmon | 604/198 |
| 5,061,251 | 10/1991 | Jahusz | 604/198 |
| 5,098,390 | 3/1992 | Wallingford | 604/195 |
| 5,104,385 | 4/1992 | Huband | 604/198 |
| 5,152,750 | 10/1992 | Haining | 604/195 |
| 5,163,907 | 11/1992 | Szuszkiewicz | 604/110 |
| 5,180,370 | 1/1993 | Gillespie | 604/110 |
| 5,188,597 | 2/1993 | Sweeney et al. | 604/110 |

FOREIGN PATENT DOCUMENTS 2137405  2/1973  Fed. Rep. of Germany ...... 604/196

Primary Examiner—C. Fred Rosenbaum
Assistant Examiner—Corrine Maglione
Attorney, Agent, or Firm—Morrison & Foerster

[57] ABSTRACT

A retractable needle is disclosed for use with a hypodermic syringe, in order to eliminate the possibility that a user could inadvertently contact a contaminated needle. The present needle comprises a hypodermic needle and needle support which can engage with the sealing portion of a commercially available hypodermic syringe plunger, allowing the needle to be withdrawn into the barrel of the syringe after use.

12 Claims, 5 Drawing Sheets

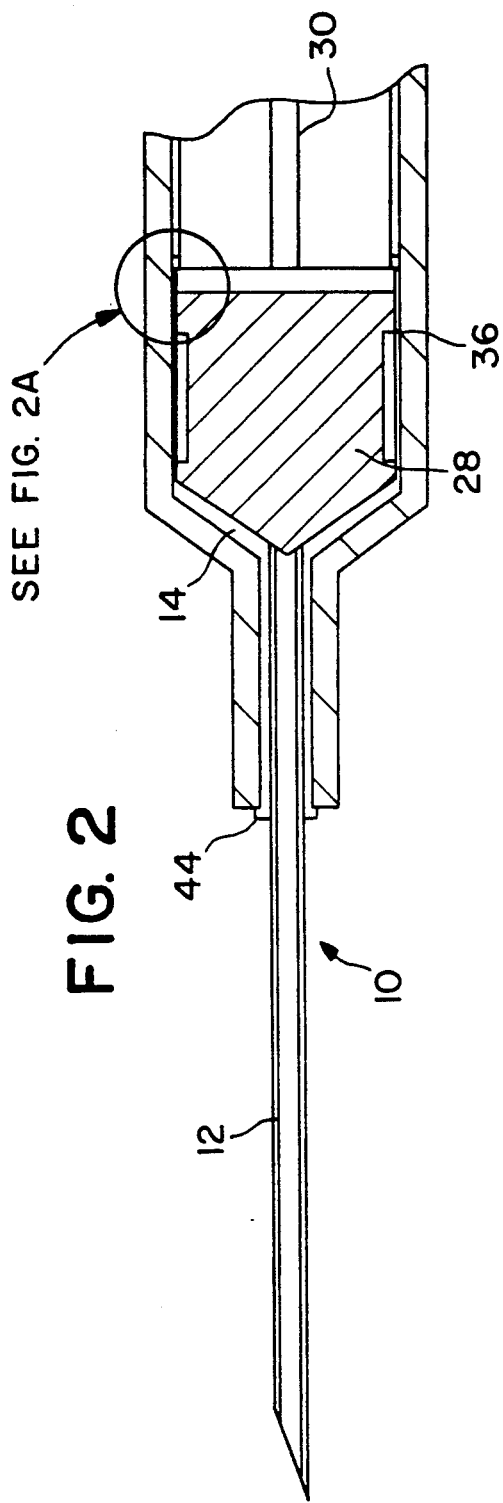
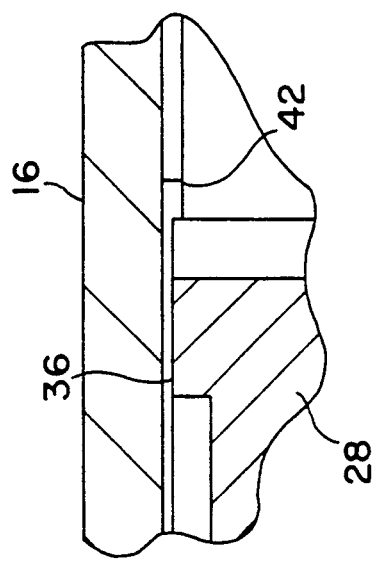

RETRACTABLE NEEDLE FOR USE WITH SYRINGE

DESCRIPTION

1. Technical Field

The present invention relates to needles used with syringes and, more particularly, to such needles which can be retracted into the barrel of the syringe after use.

2. Background of the Invention

Hypodermic syringes are common instruments utilized daily in the practice of medicine Although numerous variations exist, disposable plastic syringes are among the most frequently used. Typically, such syringes consist of a cylindrical barrel with a narrow tip at the forward end. This tip serves as a mounting point for the needle and a fluid channel for expelling the contents of the barrel. The barrel will also include flanges at the rearward end configured to provide support for the operators fingers and leverage to operate the syringe. In addition, the syringe will include a plunger with a thumb pad at the rearward end and a sealing plug or portion at the forward end. Such syringes are generally packaged aseptically, optionally with a hypodermic needle attached, and the details regarding their construction and operation are well known in the medical field.

However, once a hypodermic needle has been used, it can be contaminated with any disease vectors present in the patient. Thus, there is an ongoing concern among medical personnel to prevent the spread of infectious diseases by avoiding contact with contaminated needles. For example, concerns regarding the avoidance of infection with any of the HIV virus have provided increased emphasis on the need for such protection. Although medical personnel are generally well informed of the dangers and diligent in following proper disposal procedures, the stress of providing medical care in emergency cases inevitably causes occasional mishaps.

Therefore, it is considered desirable to provide a hypodermic syringe needle which can be quickly and easily sequestered after use to prevent further contact. One approach is to provide a hypodermic needle which can readily be withdrawn into the barrel of the syringe after use.

DESCRIPTION OF THE PRIOR ART

U.S. Pat. No. 4,969,877 is an example of a syringe which has been developed so as to allow a potentially contaminated needle to be withdrawn into the syringe after use. This disclosure involves a syringe assembly which includes an outer casing within which an inner chamber slides. A plunger having a sealing plug at one end extends into both the inner chamber and the outer casing such that the plug is secured within the interior of the inner chamber and outer casing while remaining free to slide along the length of the inner chamber. The inner chamber and outer casing are structured such that the needle can be retracted completely within the interior of the outer casing once the syringe has been used. However, this disclosure requires a specialized syringe capable of accepting the inner chamber and a plunger adapted to be fit within the inner chamber. Thus it is considered that the disclosed device would be expensive to manufacture and not readily adaptable to commercially-available disposable syringes.

In addition, U.S. Pat. No. 5,098,390 is an example of a syringe which requires a specialized plunger which contains locking lugs which must be aligned with and fitted to corresponding recesses in the needle. The plunger is rotated with respect to the barrel until the lugs engage with and lock to the recesses in the needle, in order to withdraw the needle into the barrel of the syringe. Thus there is a requirement that the lugs and recesses be placed in alignment during the process of locking the needle, a potentially complicated manipulation which can deter the user from practicing the safety feature of the invention. In addition, the various specialized features of the syringe require particular manufacturing techniques and thus the disclosed syringe also suffers from the disadvantages noted previously.

DISCLOSURE OF THE INVENTION

The present invention provides a retractable needle for use with a hypodermic syringe, in order to reduce the possibility that a user could inadvertently contact a contaminated needle.

In one embodiment, the present needle comprises a needle support means having a forward end, a rearward end configured to engage the sealing portion of a commercially available hypodermic syringe plunger, an exterior surface configured to provide slidable sealing engagement with the inner surface of the barrel of the hypodermic syringe, and an interior surface which defines an interior region of the support, which region is configured to engage with and retain the sealing portion of the plunger. A hypodermic needle is mounted on the forward end of the needle support, in fluid communication relationship with the interior region of the support and is aligned with the fluid release port of the hypodermic syringe.

In a further embodiment, the invention provides an improved hypodermic syringe having a retractable needle.

BRIEF DESCRIPTION OF THE DRAWINGS

FIGS. 2 and 2A depict cross-sectional views of the embodiment of FIG. 1 with the sealing portion of the plunger of the hypodermic syringe fitted within the interior region of the needle support, wherein FIG. 2A depicts a expanded scale cross-sectional view of a portion of a needle support which includes a feature to provide releasable positive locking engagement between the needle support and the sealing portion of the plunger; and FIGS. 3 through 5 depict cross-sectional views of the embodiment of FIG. 1 in operation in a hypodermic syringe, in which:

FIG. 3 depicts the sealing portion of the plunger of approaching the needle support;

FIG. 4 depicts the sealing portion of the plunger inserted within the interior region of the needle support; and FIG. 5 depicts the needle support and attached needle withdrawn into the barrel of the hypodermic syringe.

DETAILED DESCRIPTION OF THE INVENTION

Numerous advantages and improvements inherent in the present invention will be apparent from the present description, with reference to the hereinbelow discussed hypodermic syringe and the accompanying drawings.

In general, a commercially-available hypodermic syringe will consist of a cylindrical barrel with a convergent conical forward end. Located on the apex of this cone is a narrow tip projection which serves as a mounting point for a conventional hypodermic needle and as a fluid release port to provide a channel for expelling the liquid contents of the syringe barrel. The barrel will also include a rearward end having a plunger engagement port where the plunger is inserted into the barrel. The rearward end will also have flanges configured to provide support for the operator's fingers and leverage to operate the syringe.

In addition, the syringe will include an elongated plunger having a forward end and a rearward end, the forward end including a sealing portion configured to provide slidable fluid-sealing engagement with the inner surface of the syringe barrel. The plunger will also include a thumb pad at the rearward end, which will be used in conjunction with the flanges when the syringe is in use.

Figure 1:
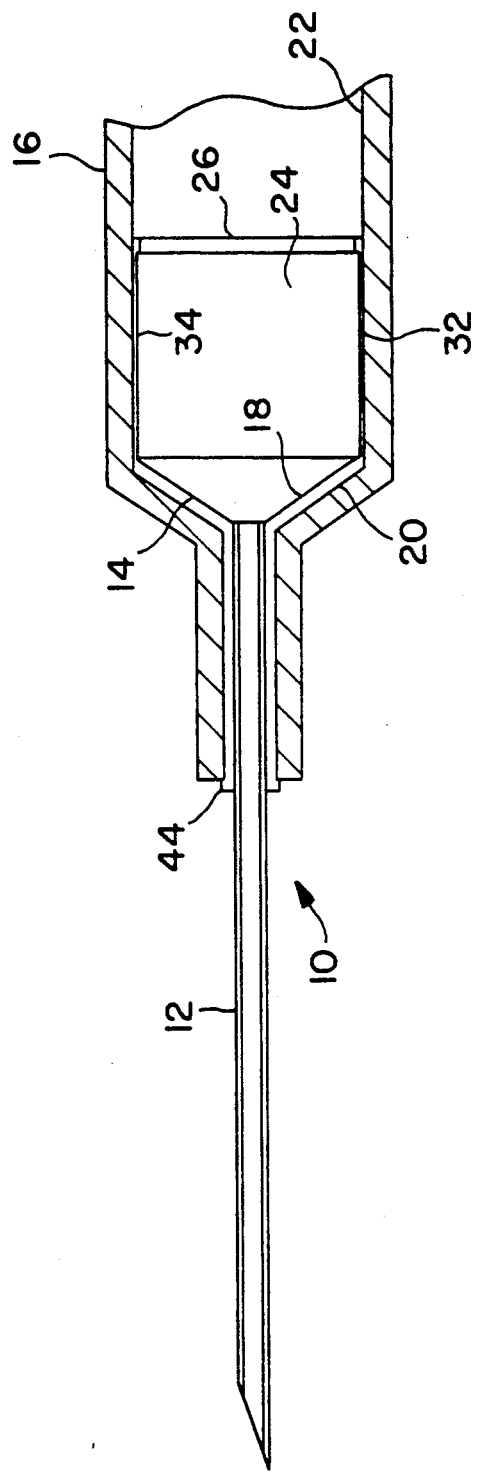
FIG. 1 depicts a cross-sectional view of one embodiment of the invention placed within the barrel of a commercially available hypodermic syringe.

As depicted in FIG. 1, one embodiment of the present invention is shown as a retractable needle 10 which comprises hypodermic needle portion 12 and needle support portion 14. The present needle can be constructed of metal, for example where needle 12 and needle support portion 14 are formed integrally, or needle support portion 14 can be formed from any rigid material to facilitate ease of manufacture. Needle support portion 14 is generally cylindrical in shape, in order to conform to the interior dimensions of syringe barrel 16, and desirably includes a conical converging forward end 18 which is adapted to establish a fluid-tight seal with forward end 20 of the interior of syringe barrel 16. Such a seal can be established, for example, by careful control of the dimensions of needle support portion 14, by including a sealing feature in the forward end 18 or by constructing needle support portion 14 of a compliant material. Needle portion 12 is securely fixed to, or releasably secured to, the forward end 18 of needle support portion 14 at the apex of the converging cone, so as to align with the fluid release port of the syringe barrel 16.

The exterior diameter of needle support portion 14 is established such that a loose interference fit will exist between the support and the interior surface 22 of syringe barrel 16. In addition, the tolerances will be established such that there exists an arrangement between needle support portion 14 and syringe barrel 16 which prevents one from sliding with respect to the other until a sufficient force is applied to the retractable needle 10.

In certain embodiments, it may be considered desirable to reduce the tendency of the needle support portion 14 to slide into the syringe barrel 16 when pressure is applied to needle 12, such as when the needle meets resistance in puncturing the skin of a patient. This objective can be accomplished, for example, by including certain structural features into retractable needle 10 in order to enhance the interlocking engagement between needle support portion 14 and barrel 16 of the syringe. For example, as depicted in FIG. 1, the portion of the needle support portion 14 which engages and surrounds needle 12 can be extended along the length of needle 12 to a point where it will project through the fluid release port and out of syringe barrel 16 when retractable needle 10 is fully engaged. The forward end of this extension can be configured with an annular ridge 44, such that the exterior diameter of the extension at ridge 44 is slightly larger than the interior diameter of the fluid release port of syringe barrel 16. In this manner, once retractable needle 10 is fully engaged with barrel 16 of the syringe, a positive locking engagement is established. This feature increases the force which would be necessary to disengage retractable needle 10 from syringe barrel 16.

As also illustrated in FIG. 1, the present needle support portion 14 will be substantially hollow so as to provide an interior region 24 which has a rearward end 26 which is essentially open and is adapted to accept the sealing portion 28 of the hypodermic syringe plunger 30. This engagement would be generally as depicted in FIG. 2.

Furthermore, interior region 24 will be provided with a fluid communication relationship with hypodermic needle 12, so that any liquid contained within syringe barrel 16 can be dispensed via interior region 24 and through needle 12 when plunger 30 is depressed.

In typical disposable syringes, sealing portion 28 of plunger 30 is preferably formed of a material which has a low co-efficient of friction, such as a nylon or rubber material. Sealing portion 28 is generally dimensioned so as to be easily slidable along the interior surface 22 of syringe barrel 16, while maintaining a fluid-tight seal. Thus, interior region 24 of needle support portion 14 will be dimensioned so that sealing portion 28 will form a tight interference fit with inner region 24 of the support.

The interference fit arrangement between the exterior surface 32 of retractable needle 10 and the interior surface 22 of syringe barrel 16, the optional positive locking engagement feature described above, as well as the types of the materials chosen for their construction, allow for the achievement of a predetermined value in the force required to disengage retractable needle 10 from syringe barrel 16.

In like manner, design and construction parameters of retractable needle 10 provide the means to adjust the value of the force required to engage sealing portion 28 of plunger 30 with interior region 24 of needle support portion 14. Thus, the relatively tight interference fit between the sealing portion 28 of the plunger and the inner surface 34 of interior region 24 of retractable needle 10 provides that a relatively high force will be necessary to break the frictional bond between these elements, as compared to the frictional bond between outer surface 32 of needle support portion 14 and inner surface 22 of syringe barrel 16.

The force required to initiate movement between needle support portion 14 and inner surface 22 of the syringe barrel ($F_1$) will be of a value lesser than that of the force required to initiate movement between sealing portion 28 of plunger 30 and inner surface 34 of interior region 24 of needle support portion 14 ($F_2$). To insure a sufficient difference between $F_1$ and $F_2$ so that retractable needle 10 will reliably retract into syringe barrel 16 after use, various means are available. For instance, roughening either interior surface 34 of needle support portion 14 or exterior surface 36 of sealing portion 28 of plunger 30 would result in a higher force value. It is considered desirable to effect such a modification on needle support portion 14, in order to readily adapt the present device to a wide range of commercially-available syringes without requiring modification thereof. Such roughening of interior surface 34 can be achieved in any conventional means, such as mechanically, chemically or by various well-known molding techniques, which produce a textured surface.

Alternatively, certain structural features can be incorporated into retractable needle 10 in order to enhance the interlocking engagement between needle support portion 14 and the sealing portion 28 of the plunger. For example, as depicted in FIG. 2A, interior region 24 of needle support portion 14 can be configured with an annular ridge 42 at the rearmost edge 26, such that the interior diameter of needle support portion 14 at ridge 42 is smaller than that of sealing portion 28 of plunger 30. The remaining diameter of interior region 24 of needle support portion 14 will be sufficient to accept the compressed sealing portion 28 of plunger 30. In this manner, once sealing portion 28 of plunger 30 is engaged in interior region 24 of needle support portion 14, a positive locking engagement is established. This feature greatly increases the force ($F_2$) which would be necessary to disengage plunger 30 from retractable needle 10.

Figure 3:
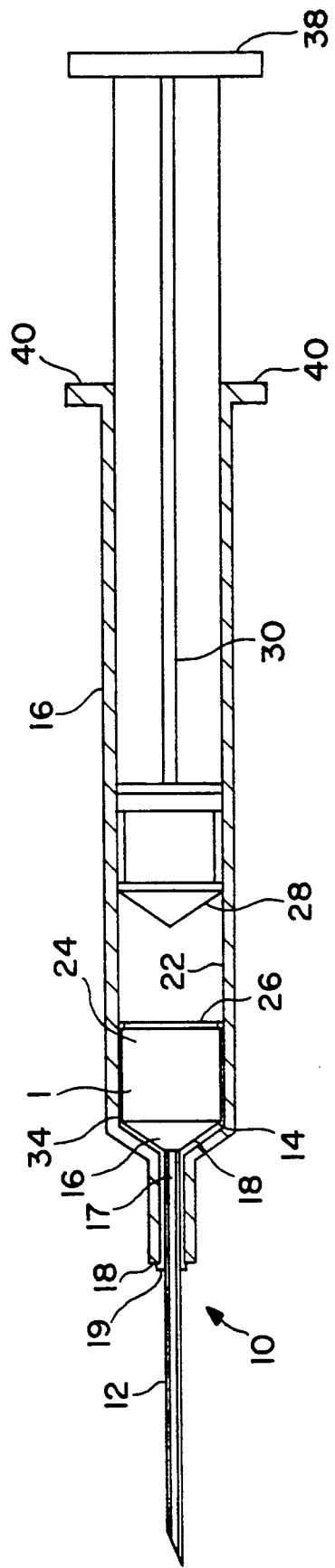

As shown in FIG. 3, plunger 30 with attached sealing portion 28 extends into syringe barrel 16 in such fashion that sealing portion 28 makes fluid sealing engagement with inner surface 22 of barrel 16. Plunger 30 is of sufficient length to allow sealing portion 28 to extend into inner region 24 of needle support portion 14 before the syringe thumb pad 38 comes in contact with flanges 40.

In use, the retractable needle 10 of the present invention can be installed in the syringe at the site of manufacture and hypodermic needle 12 can be covered with any conventional needle guard. The syringe can then be shipped with sealing portion 28 of plunger 30 positioned within barrel 16 of the syringe, but not inserted into inner region 24 of needle support portion 14.

The operation of the present invention will be described with reference to FIGS. 3 through 5. As shown in FIG. 3, withdrawal of plunger 30 with attached sealing portion 28 is possible without establishing a locking engagement between sealing portion 28 and interior region 24 of the retractable needle 10. Once the desired amount of fluid is drawn into syringe barrel 16, and any undesired air is subsequently expelled, plunger 30 will be pressed forward, causing the fluid to pass from the interior of barrel 16 through needle support portion 14 and hypodermic needle 12.

Figure 4:
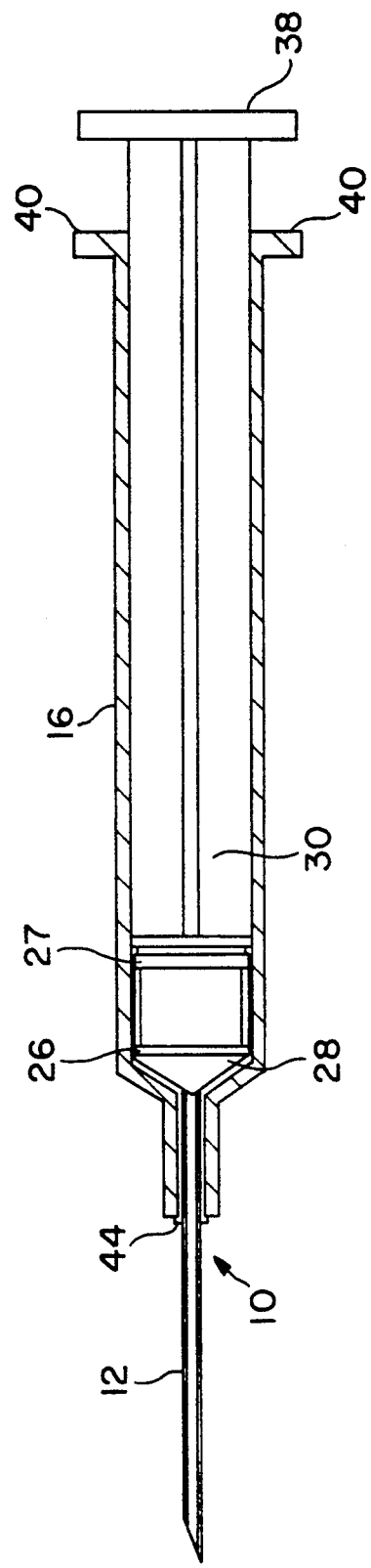
Figure 5:
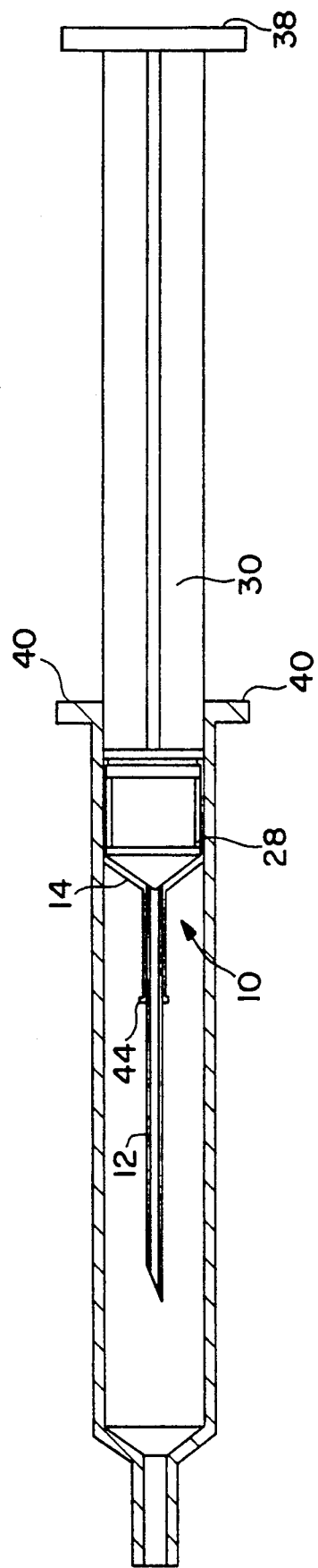

The final portion of fluid would then be expelled by pressing plunger 30 with sufficient force to insert sealing portion 28 into interior region 24 of needle support portion 14, as shown in FIG. 4. FIG. 5 then shows that, once this engagement is established, the plunger can be withdrawn with a force greater than $F_1$ but less than $F_2$ so as to draw needle support portion 14 and attached hypodermic needle 12 into syringe barrel 16 for subsequent disposal.

Thus it can be seen that the present invention provides a novel and improved retractable needle for use with commercially-available syringes, providing for safe disposal while minimizing the risk of inadvertent contact with a contaminated needle. In addition, the present needle can be constructed and assembled in a manner which readily adapts to commercially-available syringe technology.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity and understanding, it will be apparent to those of ordinary skill in the art in light of the teaching of this invention that certain changes and modifications may be made thereto without departing from the spirit or scope of the appended claims.

We claim:

1. A retractable needle for use with a hypodermic syringe which syringe includes (i) a substantially cylindrical barrel and (ii) a plunger having a compressible, substantially cylindrical sealing portion, said needle comprising:
   a needle support means comprising a forward end, a rearward end configured to engage the sealing portion of the plunger, an exterior surface configured to provide slidable sealing engagement with the inner surface of the syringe barrel and an interior surface which defines an interior region of said needle support means, which region is configured to engage with and retain the sealing portion of the plunger in a frictional engagement; and
   a hypodermic needle mounted on said needle support in a fluid-communicating relationship with said interior region of said needle support means but not extending into said interior region.

2. A retractable needle as recited in claim 1, wherein the interior surface of the needle support means further comprises an annular ridge at the rearward end which has a smaller inner diameter than the diameter of the sealing portion of the plunger, thereby providing positive engagement between the sealing portion of the plunger and the interior region of the needle support means.

3. A retractable needle as recited in claim 1 wherein the forward end of the needle support means further comprises an extended portion capable of projecting through and engaging a fluid release channel of a hypodermic syringe barrel, thereby providing positive engagement between the retractable needle and the syringe barrel.

4. A retractable needle as recited in claim 3, wherein said extended portion of the needle support means includes an annular ridge at the forward end which has a larger outer diameter than the inner diameter of the fluid release channel, so that the needle support means is capable of releasable locking engagement with the syringe barrel.

5. A syringe having a retractable hypodermic needle, comprising a barrel, a plunger and a needle support means;
   (a) said barrel being elongated, substantially cylindrical and having a forward end including a fluid release port, a rearward end including a plunger engagement port, an exterior surface and an interior surface which defines a first interior region;
   (b) said plunger being elongated and configured to engage with said plunger engagement port, and having a forward end and a rearward end, said forward end further comprising a sealing portion configured to provide slidable sealing engagement with the inner surface of said barrel and to provide a retaining engagement with the needle support means; and
   (c) said needle support means comprising:
   (i) a forward end further comprising a hypodermic needle aligned with said fluid release port, (ii) a rearward end configured to engage the sealing portion of said plunger, (iii) an exterior surface configured to provide slidable sealing engagement with the inner surface of said barrel, and (iv) an interior surface which defines a second interior region configured to engage with and retain the sealing portion of said plunger in a frictional engagement, said second interior region having a fluid communication relationship with the needle, wherein said needle does not extend into said interior region.

6. A syringe according to claim 5 wherein the interior surface of the needle support means further comprises an annular ridge at the rearward end which has a smaller inner diameter than the diameter of the sealing portion of the plunger, thereby providing positive engagement between the sealing portion of the plunger and the interior region of the needle support means.

7. A syringe according to claim 5 wherein the forward end of the needle support means further comprises an extended portion capable of projecting through and engaging the fluid release channel of the syringe barrel, thereby providing positive engagement between the needle support means and the syringe barrel.

8. A syringe according to claim 7 wherein the extended portion of the needle support means includes an annular ridge at the forward end which has a larger outer diameter than the inner diameter of the fluid release channel, so that the support means is capable of releasable locking engagement with the syringe barrel.

9. In a syringe having an elongated substantially cylindrical barrel with a forward end including a fluid release port, a rearward end including a plunger engagement port, an exterior surface and an interior surface defining a first interior region, said syringe further having an elongated plunger configured to engage with said plunger engagement port, and having a forward end and a rearward end, said forward end further comprising a sealing portion configured to provide slidable sealing engagement with the inner surface of said barrel; the improvement comprising a needle support means comprising:

(a) a forward end further comprising a hypodermic needle aligned with the syringe fluid release port, (b) a rearward end configured to engage the sealing portion of the plunger, (c) an exterior surface configured to provide slidable sealing engagement with the inner surface of the barrel, and (d) an interior surface which defines a second interior region configured to engage with and retain the sealing portion of the plunger in a frictional engagement, said second interior region having a fluid communication relationship with the hypodermic needle, wherein said needle does not extend into said second interior region.

10. A syringe as recited in claim 9 wherein the interior surface of the needle support means further comprises an annular ridge at the rearward end which has a smaller inner diameter than the diameter of the sealing portion of the plunger, thereby providing positive engagement between the sealing portion of the plunger and the interior region of the needle support means.

11. A syringe as recited in claim 9 wherein the forward end of the needle support means further comprises an extended portion capable of projecting through and engaging the fluid release channel of the syringe barrel, thereby providing positive engagement between the needle support means and the syringe barrel.

12. A syringe as recited in claim 11 wherein said extended portion of the needle support means includes an annular ridge at the forward end which has a larger outer diameter than the inner diameter of the fluid release channel, so that the needle support means is capable of releasable locking engagement with the hypodermic syringe barrel.

* * * * *